United States Patent [19]

Takago et al.

[11] Patent Number: 5,227,502
[45] Date of Patent: Jul. 13, 1993

[54] FLUORINATED GLYCIDYL ETHERS AND METHOD OF MAKING

[75] Inventors: Toshio Takago; Hiroshi Inomata; Yasuo Tarumi; Hiromasa Yamaguchi; Kenichi Fukuda, all of Gunma, Japan

[73] Assignee: Shin-Etsu Chemical Co., Ltd., Tokyo, Japan

[21] Appl. No.: 922,424

[22] Filed: Jul. 31, 1992

[30] Foreign Application Priority Data

Jul. 31, 1991 [JP] Japan .................................. 3-214670
Jul. 31, 1991 [JP] Japan .................................. 3-214671
Jul. 31, 1991 [JP] Japan .................................. 3-214672

[51] Int. Cl.$^5$ .................. C07D 301/28; C07D 303/22
[52] U.S. Cl. .................................... 549/558; 549/215; 549/516
[58] Field of Search ............................... 549/558

[56] References Cited

U.S. PATENT DOCUMENTS

| | | | |
|---|---|---|---|
| 3,361,685 | 1/1968 | Pittman et al. | 549/558 |
| 3,417,035 | 12/1968 | Elmer et al. | 549/558 |
| 3,616,462 | 10/1971 | Gurgiolo et al. | 549/558 |

FOREIGN PATENT DOCUMENTS

| | | | |
|---|---|---|---|
| 2333934 | 1/1974 | Fed. Rep. of Germany | 549/558 |
| 2287432 | 5/1976 | France | 549/558 |

*Primary Examiner*—Joseph E. Evans
*Attorney, Agent, or Firm*—Millen, White, Zelano & Branigan

[57] ABSTRACT

Novel fluorinated unsaturated glycidyl ethers are prepared by reacting 1,1,1-trifluoro-2-trifluoromethyl-3-buten-2-ol or 1,1,1-trifluoro-2-trifluoromethyl-4-propen-2-ol with chloromethyloxirane in the presence of onium salts. The fluorinated unsaturated glycidyl ethers are, in turn, subject to addition reaction with hydrosilanes in the presence of transition metal catalysts, obtaining novel silicon-modified glycidyl ethers or fluorinated organic silicon compounds.

1 Claim, 2 Drawing Sheets

FLUORINATED GLYCIDYL ETHERS AND METHOD OF MAKING

This invention relates to novel fluorinated glycidyl ethers including fluorinated unsaturated glycidyl ethers and silicon-modified fluorinated glycidyl ethers and methods for preparing the same.

BACKGROUND OF THE INVENTION

One prior art well-known ether compound having a vinyl group and an oxirane ring in its molecule is allyl glycidyl ether of the following formula (see Bailschtain, Third and Fourth Ed., Vol. 17, page 990).

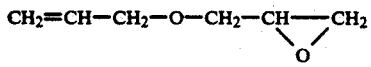

Because of its reactivity, this allyl glycidyl ether has been widely used in the industrial field as a monomer for the preparation of a homopolymer or a copolymer with a compound having a carbon-to-carbon double bond, an intermediate reactant intended for silane coupling agents along with various silanes, a crosslinking agent for epoxy resins, and an intermediate reactant for forming resin monomers.

Polymers and other products resulting from allyl glycidyl ether are low in water repellency, moisture resistance and compatibility with fluorinated materials. There is a need for imparting or improving such properties.

Also known in the prior art are epoxy-modified silanes of the following formula:

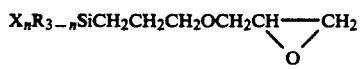

wherein X is a hydrolyzable group, R is a monovalent organic group, and n is an integer of 1 to 3. These compounds contain a X—Si group reactive with glass, metal, silica, quartz sand, etc. and an epoxy group reactive with an alcohol, amino or carboxyl group of organic resins in the same molecule so that they are very effective in increasing the mechanical strength and electrical properties of epoxy resin/glass laminates, phenolic resin/glass laminates and phenolic resin shell molds. Treatment of silica with these compounds can modify the silica surface with an epoxy group-containing residue. However, these epoxy-modified silanes sometimes fail to provide sufficient water resistance and heat resistance, and leave the possibility of decomposition of an ether linkage in their molecule.

SUMMARY OF THE INVENTION

An object of the present invention is to provide a novel fluorinated unsaturated glycidyl ether which when products such as a homopolymer, copolymer or carbon-functional silane (e.g., silane coupling agent) are prepared therefrom, imparts or improves physical properties such as water repellency, moisture resistance and compatibility with other fluorinated materials which have never been available with products derived from allyl glycidyl ether.

Another object is to provide a method for preparing such a fluorinated unsaturated glycidyl ether.

A further object is to provide a silicon-modified fluorinated glycidyl ether which is effective in improving the strength and electrical properties of laminates based on epoxy resins and phenolic resins and in modifying the surface of silica fillers and which when used in such application, can impart fluorinated compounds' inherent properties such as water resistance, heat resistance and low surface energy to resins and fillers.

A still further object is to provide a method for preparing such a silicon-modified fluorinated glycidyl ether.

The inventors have found that as shown by the following scheme A, by reacting a compound of the following formula (3) (that is, 1,1,1-trifluoro-2-trifluoromethyl-3-buten-2-ol or 1,1,1-trifluoro-2-trifluoromethyl-4-penten-2-ol) with chloromethyloxirane in the presence of at least one onium salt selected from the group consisting of quaternary ammonium salts and quaternary phosphonium salts in a two phase system of a basic aqueous phase and an organic phase, there is obtained a novel fluorinated unsaturated glycidyl ether of the following formula (1) having a trifluoromethyl group incorporated therein. This fluorinated unsaturated glycidyl ether is a useful monomer for the preparation of a homopolymer and copolymers with compounds having a carbon-to-carbon double bond, as well as a useful reactant for the preparation of carbon functional silanes and other products.

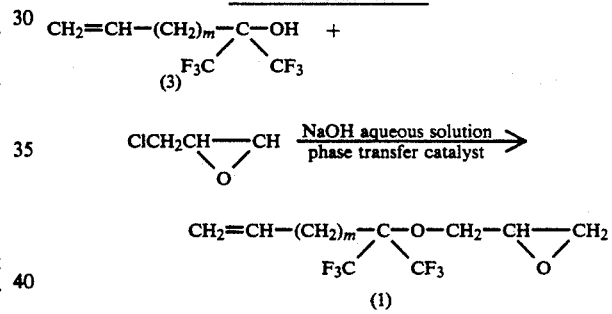

m = 0 or 1

The fluorinated unsaturated glycidyl ether of formula (1) according to the present invention can be used as a reactant for the preparation of various products by taking advantage of its reactivity since it contains a vinyl group and oxirane ring, both reactive, at its molecular ends like allyl glycidyl ether. For example, a homopolymer is obtained when the present compound is polymerized alone. Copolymers are obtained when it is polymerized with other compounds having a carbon-to-carbon double bond or vinyl monomers. Carbon functional silanes such as silane coupling agents are obtained when various silanes are reacted to the present compound. Since the fluorinated unsaturated glycidyl ether according to the present invention contains trifluoromethyl groups in a molecule in addition to a vinyl group and oxirane ring, it can impart to the above-mentioned products novel physical properties such as water and oil repellency, low surface tension, heat resistance, low refractive index, moisture resistance and compatibility with other fluorinated materials which have never been available with products derived from allyl glycidyl ether, that is, achieve significant improvements in such properties over the allyl glycidyl ether-derived products. Accordingly, the present compound is capable of imparting and/or improving these physical properties and can be utilized in deriving various other fluorinated compounds therefrom. Because of the inclusion of an oxirane ring, the fluorinated unsaturated glycidyl ether of the present invention is also useful as a curing agent for epoxy resin and an intermediate reactant for various resin monomers.

Also the inventors have found that as shown by the following reaction scheme B, by starting with the compound of formula (1), a novel fluorinated organic silicon compound or silicon-modified glycidyl ether of the following formula (2) is obtained. Since this novel fluorinated organic silicon compound of formula (2) contains a X—Si group and an epoxy group in the same molecule like the prior art epoxy-modified silanes, it is effective for reinforcing the bond of epoxy and phenolic resins to inorganic materials such as glass, silica, metal, and quartz sand, contributes to improvements in mechanical strength and electrical properties of such composite materials. In addition, the CF$_3$ groups in the molecule are effective in further improving water resistance and heat resistance. By treating silica with the compound of formula (2), the silica can be not only modified on the surface with an epoxy-functional residue, but also improved in water resistance by virtue of CF$_3$ groups, thus imparting affinity to fluororesins and fluororubbers. Moreover, since the compound of formula (2) according to the present invention contains two CF$_3$ groups on the carbon at alpha-position of the ether bond, the ether bond is shielded so that the tendency of decomposition at this site is retarded.

Reaction scheme B:

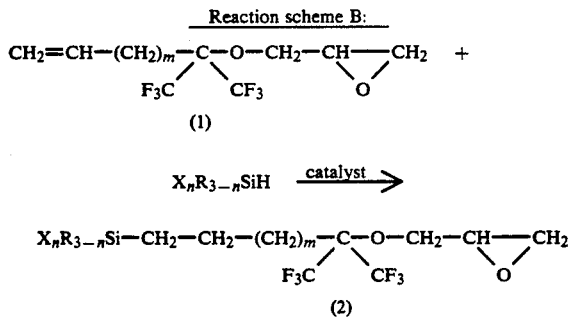

Catalyst: a transition metal, salt or complex thereof
X: a hydrolyzable group
R: a monovalent organic group
n: an integer of 1 to 3
m: 0 or 1

Consequently, the present invention provides fluorinated glycidyl ethers of formula (1) and (2) and methods for preparing the same.

DETAILED DESCRIPTION OF THE INVENTION

Figure 1:
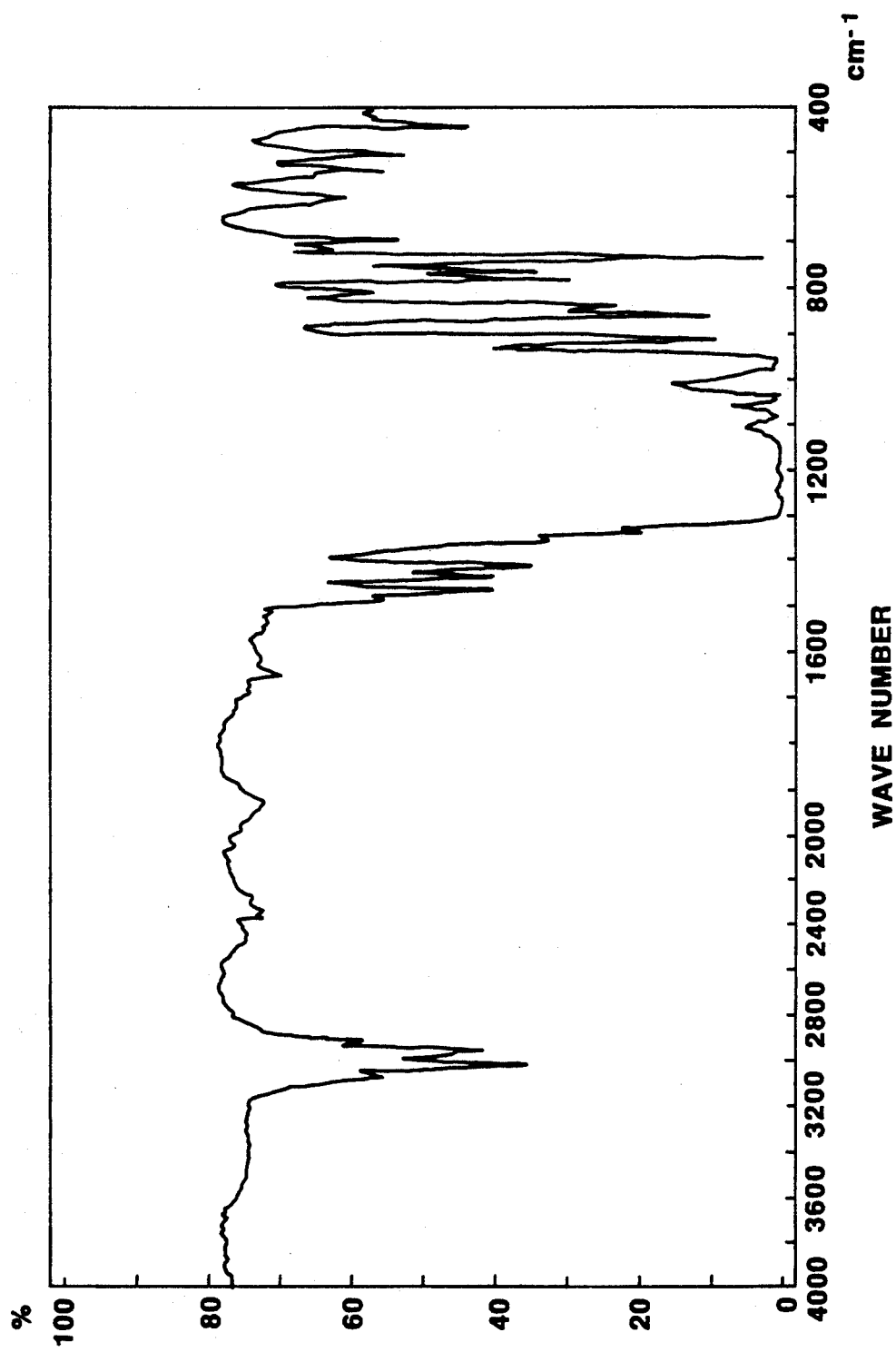
FIG. 1 is an IR absorption spectrum of the fluorinated glycidyl ether prepared in Example 1.
Figure 2:
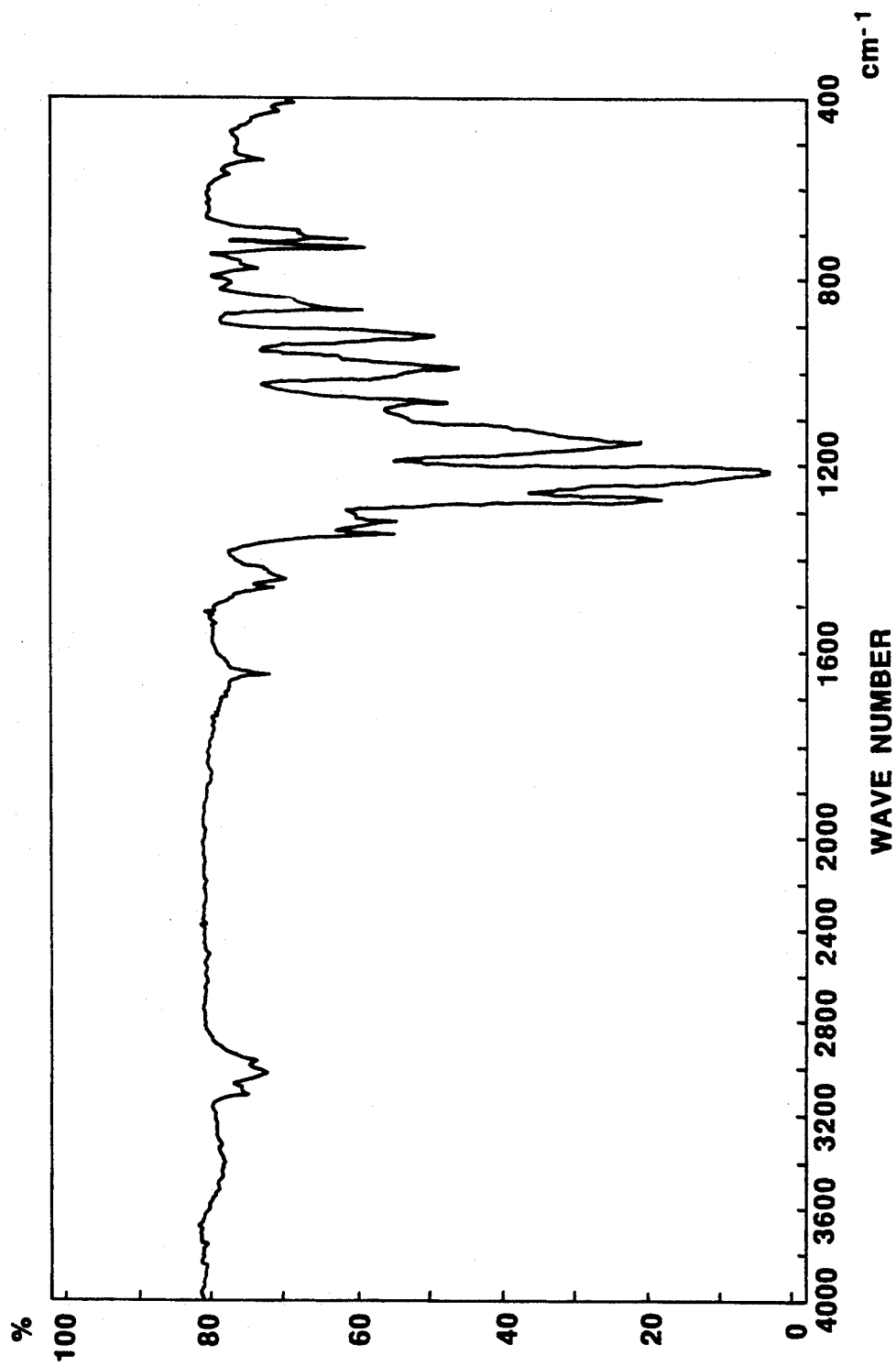
FIG. 2 is an IR absorption spectrum of the fluorinated glycidyl ether prepared in Example 3.

The fluorinated glycidyl ether in a first form of the present invention is a fluorinated unsaturated glycidyl ether of the following formula (1).

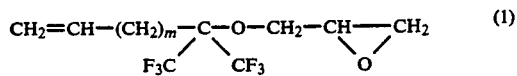

Letter m is equal to 0 or 1. Included in formula (1) are a compound of formula (1a) wherein m=0 and a compound of formula (1b) wherein m=1.

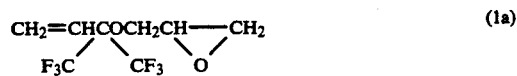

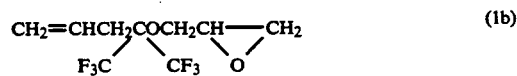

The fluorinated unsaturated glycidyl ethers of formula (1) according to the present invention are novel useful compounds in that when products such as a homopolymer copolymer or carbon functional silane are prepared therefrom, they can impart to the products physical properties such as water repellency, moisture resistance and compatibility with other fluorinated materials which have never been available with the prior art allyl glycidyl ether-derived products. They are also useful as crosslinking agents for epoxy resins and intermediate reactants for forming various resin monomers.

The compounds of formula (1) can be prepared by reacting compounds of the following formula (3):

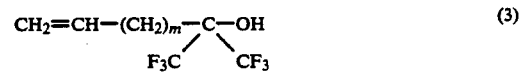

wherein m is equal to 0 to 1 with chloromethyloxirane in the presence of at least one onium salt selected from the group consisting of quaternary ammonium salts and quaternary phosphonium salts in a two phase system of a basic aqueous phase and an organic phase.

Among the compounds of formula (3) which are one of the starting reactants used in this method, one compound of formula (3) wherein m=0 is a known compound designated 1,1,1-trifluoro-2-trifluoromethyl-3-buten-2-ol and may be readily prepared by reacting vinyl magnesium bromide with hexafluoroacetone, for example. The other compound of formula (3) wherein m=1 is also a known compound designated 1,1,1-trifluoro-2-trifluoromethyl-4-penten-2-ol and may be readily prepared by reacting propene with hexafluoroacetone, for example.

Another starting reactant is chloromethyloxirane which is a known compound and may be readily prepared in a conventional manner.

For reaction, the compound of formula (3) and chloromethyloxirane are generally used in a molar ratio of from about 1:1 to about 1:50, preferably from about 1:2 to about 1:10.

The basic aqueous phase used in the method may be selected from aqueous solutions of alkali metal hydroxides such as sodium hydroxide and potassium hydroxide and aqueous solutions of alkaline earth metal hydroxides such as calcium hydroxide, with aqueous solutions of sodium hydroxide, potassium hydroxide and calcium hydroxide being preferred. The basic aqueous solution generally has a concentration of from about 5% by weight to saturation, preferably from about 10 to 30% by weight. The amount of the base used may be selected in the range of about 0.1 to 10 equivalents, preferably about 0.5 to 2 equivalents relative to the compound of formula (3).

In the method of the present invention, an onium salt selected from the group consisting of quaternary ammonium salts and quaternary phosphonium salts is used as a phase transfer catalyst. The quaternary ammonium salts are salts of quaternary ammonium ions with anions. Examples of the quaternary ammonium ion include tetramethylammonium ion, tetraethylammonium ion, tetra-n-propylammonium ion, tetra-n-butylammonium ion, tri-n-octylmethylammonium ion, cetyltrimethylammonium ion, benzyltrimethylammonium ion, benzyltriethylammonium ion, cetylbenzyldimethylammonium ion, cetylpyridinium ion, n-dodecylpyridinium ion, phenyltrimethylammonium ion, phenyltriethylammonium ion, N-benzylpicolinium ion, pentamethonium ion, hexamethonium ion, etc. Examples of the anion include chloride ion, bromide ion, fluoride ion, iodide ion, hydrogen sulfate ion, sulfate ion, phosphate ion, nitrate ion, hydroxy ion, acetate ion, benzoate ion, benzenesulfonate ion, p-toluenesulfonate ion, etc.

The quaternary phosphonium salts are salts of quaternary phosphonium ions with anions. Examples of the quaternary phosphonium ion include tetraethylphosphonium ion, tetra-n-butylphosphonium ion, tri-n-octylethylphosphonium ion, cetyltriethylphosphonium ion, cetyltri-n-butylphosphonium ion, n-butyltriphenylphosphonium ion, n-amyltriphenylphosphonium ion, n-hexyltriphenylphosphonium ion, n-heptyltriphenylphosphonium ion, methyltriphenylphosphonium ion, benzyltriphenylphosphonium ion, tetraphenylphosphonium ion, etc. Exemplary anions are the same as described for the anions of the quaternary ammonium salts.

These onium salts may be used alone or in admixture of two or more, generally in an amount of about 0.001 to 1 mol, preferably about 0.01 to 0.1 mol per mol of the compound of formula (3).

In the practice of the invention, reaction may be carried out by concurrently charging a reactor with the two reactants, onium salt and basic aqueous solution, or by previously charging a reactor with one to three components and subsequently adding the remaining components to the reactor. Most often, a reactor is charged with the two reactants and onium salt and heated to the reaction temperature before the basic aqueous solution is added dropwise to the reactor.

The reaction conditions include a temperature of $-25°$ C. to $100°$ C., preferably $30°$ C. to $95°$ C., more preferably $50°$ C. to $90°$ C. and a time of 10 minutes to 8 hours, preferably 30 minutes to 2 hours.

The fluorinated glycidyl ether in a second form of the present invention is a fluorinated silicon compound or silicon-modified fluorinated glycidyl ether of the following formula (2).

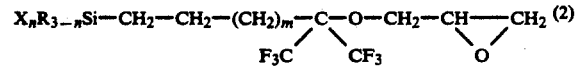

In formula (2), X is a hydrolyzable group, R is a monovalent organic group, n is an integer of 1 to 3, and m is equal to 0 or 1.

The hydrolyzable group represented by X is preferably selected from the group consisting of F, Cl, Br, I, $OR^1$ and $NR^2R^3$. $R^1$ is an organic group including alkyl groups having 1 to 10 carbon atoms such as methyl, ethyl, n-propyl, i-propyl and n-butyl groups, fluoroalkyl groups having 2 to 15 carbon atoms such as a trifluoroethyl group, acyl groups such as acetyl and propionyl groups, and alkenyl groups having 2 to 5 carbon atoms such as an isopropenyl group. $R^2$ and $R^3$, which may be the same or different, are alkyl groups having 1 to 10 carbon atoms such as methyl, ethyl, and isopropyl groups.

The organic group represented by R is selected from alkyl groups having 1 to 10 carbon atoms such as methyl, ethyl, and n-propyl groups, aryl groups having 6 to 10 carbon atoms such as phenyl and tolyl groups, and fluoroalkyl groups having 3 to 15 carbon atoms such as a trifluoropropyl group.

Preferred among the compounds of formula (2) are those wherein X is a lower alkoxy group such as a methoxy, ethoxy and isopropenoxy group and R is a lower alkyl group such as a methyl group. Preferred examples are fluorinated organic silicon compounds of the following formulae (2a) and (2b).

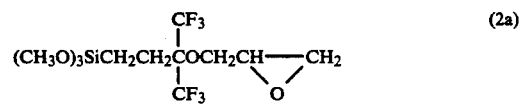

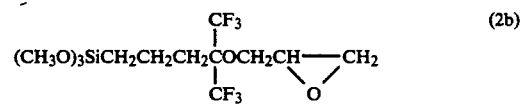

The compound of formula (2) can be synthesized by effecting addition reaction between a fluorinated unsaturated glycidyl ether of formula (1) defined above and a hydrosilane of the following formula (3):

wherein X, R and n are as defined above in the presence of a transition metal or a salt or complex thereof as a catalyst.

The amounts of the fluorinated unsaturated glycidyl ether of formula (1) and the hydrosilane of formula (4) are not particularly limited although they are preferably used in a molar ratio of from about 1:0.8 to about 1:2, more preferably from about 1:1 to about 1:1.5.

For promoting reaction between the compounds of formula (1) and (4), a transition metal such as Pt, Rh and Pd, a transition metal salt or a transition metal complex is used as a catalyst alone or in admixture of two or more. Examples of the catalyst include $H_2PtCl_6$, complexes of $H_2PtCl_6$ with olefins, complexes of $H_2PtCl_6$ with alcohols, complexes of $H_2PtCl_6$ with vinylsiloxanes, $RhCl_3$, $Rh(CH_2COCHCOCH_2)_3$, $Rh(PPh_3)_3Cl$, $Rh(PPh_3)_3Br$, $Rh_2(AcO)_4$, $Rh(PPh_3)_2(CO)Cl$, $Rh(CH_2COCHCOCH_2)(CO)_2$, $Rh_4(CO)_{12}$, $Rh_6(CO)_{16}$, $Rh(PPh_3)_3(CO)H$, $(NH_4)_2PdCl_6$, $(NH_4)_2PdCl_4$, $Pd(CH_2COCHCOCH_2)_2$, $Pd(PhCN)_2Cl_2$, $Pd(PPh_3)_2Cl_2$, $Pd(PPh_3)_4$, etc. wherein Ph is phenyl, and Ac is acetyl.

As compared with conventional olefins, the reactant of formula (1), especially that of formula (1a) is less susceptible to addition reaction of Si—H to its double bond due to the steric and electronic effects of the two $CF_3$ groups. This problem is effectively overcome by the use of the catalyst, especially rhodium complexes such as $Rh(CH_2COCHCOCH_2)_3$, $Rh(PPh_3)_3Cl$, $Rh(PPh_3)_3Br$, $Rh(PPh_3)_2(CO)Cl$, and $Rh_2(AcO)_4$.

Even when H₂PtCl₆ and modified catalysts thereof are least effective to produce the end adduct, the rhodium catalysts permit formation of the end adduct under practically acceptable temperature and time conditions.

Generally, the amount of the catalyst used is about $1\times10^{-2}$ to $1\times10^{-6}$ mol, preferably about $1\times10^{-3}$ to $1\times10^{-5}$ mol per mol of the hydrosilane.

This reaction may or may not use a solvent and generally proceeds smoothly in a solvent-free system.

The reaction may be carried out by charging a reactor with the hydrosilane and catalyst and subsequently adding dropwise the fluorinated unsaturated glycidyl ether to the reactor. Alternatively, a reactor may be first charged with the fluorinated unsaturated glycidyl ether and catalyst before the hydrosilane is added dropwise. It is also possible to charge a reactor with the two reactants and catalyst and subsequently heat the reactor to a sufficient temperature for reaction to proceed. In any case, temperature control is necessary since the reaction is exothermic. The reaction temperature is generally about 30° to 200° C., preferably about 60° to 150° C. and the reaction time generally ranges from about 30 minutes to 48 hours. The reaction can be tracked by gas chromatography which ensures monitoring of reactant consumption and end product formation. If reactant consumption stops midway the reaction process, the reaction can be effectively restarted by feeding an additional catalyst. The reaction product may be purified and isolated by distillation.

EXAMPLE

Examples of the present invention are given below by way of illustration and not by way of limitation. All percents are by weight unless otherwise stated.

Example 1

A 500-ml three-necked flask equipped with a condenser, dropping funnel, thermometer, and magnetic stirrer was charged with 108.5 grams (0.55 mol) of 1,1,1-trifluoro-2-trifluoromethyl-3-buten-2-ol, 254.4 grams (2.75 mol) of chloromethyloxirane, and 18.7 grams (0.055 mol) of tetrabutylammonium hydrogen sulfate. With stirring, the mixture was heated to 70° C. To the flask 146.7 grams (0.55 mol) of an aqueous solution of 15% by weight sodium hydroxide was added dropwise over about 1.5 hours and the mixture was stirred for a further 30 minutes. The reaction solution was allowed to cool to room temperature and separated into an organic layer and an aqueous layer. The organic layer was twice washed with water and dried over 30.0 grams of anhydrous sodium sulfate. After the excess chloromethyloxirane was distilled off, vacuum distillation yielded 89.4 grams of the end product, that is, fluorinated allylglycidyl ether of formula (1a). This product had a boiling point of 81°–82° C./65 Torr and a yield of 65.0%.

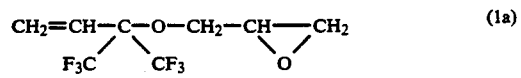
(1a)

This fluorinated allylglycidyl ether was analyzed by proton-NMR spectroscopy, IR spectroscopy, mass spectroscopy and elemental analysis, with the following results. The IR spectrum is shown in FIG. 1.

Analytical results

¹H-NMR (CCl₄ solution, TMS internal standard, ppm):

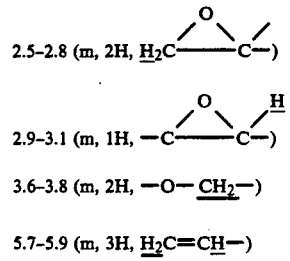

2.5–2.8 (m, 2H, H₂C—C—)

2.9–3.1 (m, 1H, —C—C—)

3.6–3.8 (m, 2H, —O—CH₂—)

5.7–5.9 (m, 3H, H₂C=CH—)

IR (KBr plate method, neat, cm⁻): 3010, 2940, 1920, 1645, 1465, 1435, 1410, 1300-1150, 1030, 960, 915, 860, 735

MS (m/e): 251 (m+1), 233, 221, 73

| | Elemental analysis: | | |
|---|---|---|---|
| | C | H | F |
| Calcd. (%) | 38.4 | 3.2 | 45.6 |
| Found (%) | 38.6 | 3.1 | 45.4 |

Example 2

A mixture of 1.0 gram (5.2 mmol) of 1,1,1-trifluoro-2-trifluoromethyl-3-buten-2-ol, 2.4 grams (25.9 mmol) of chloromethyloxirane, 1.4 grams (5.3 mmol) of an aqueous solution of 15% by weight sodium hydroxide, and 0.5 mmol of the phase transfer catalyst shown in Table 1 was heated at 80° C. for 2 hours and then analyzed for composition by gas chromatography. The results are shown in Table 1.

TABLE 1

Synthesis of fluorinated allylglycidyl ethers using phase transfer catalysts

| | Conversion of CH₂=CH—C(F₃C)(CF₃)—OH (%) | Yield* of CH₂=CH—C(F₃C)(CF₃)—O—CH₂CH—CH₂ (with epoxide) (%) |
|---|---|---|
| (n-C₄H₉)₄NCl | 88 | 66 |
| (n-C₄H₉)₄NBr | 84 | 69 |
| C₆H₅CH₂(CH₃)₃NCl | 92 | 73 |
| 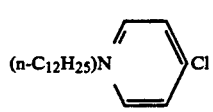 (n-C₁₂H₂₅)N⟨pyridinium⟩Cl | 66 | 45 |

TABLE 1-continued

| Synthesis of fluorinated allylglycidyl ethers using phase transfer catalysts | | |
|---|---|---|
| | Conversion of $CH_2=CH-\underset{\underset{CF_3}{F_3C}}{\overset{\phantom{x}}{C}}-OH$ (%) | Yield* of $CH_2=CH-\underset{\underset{CF_3}{F_3C}}{\overset{\phantom{x}}{C}}-O-CH_2CH\overset{O}{\underset{\phantom{x}}{-}}CH_2$ (%) |
| $(n-C_4H_9)_4PBr$ | 58 | 53 |

*calculated based on the consumed amount of $CH_2=CH-\underset{\underset{CF_3}{F_3C}}{\overset{\phantom{x}}{C}}-OH$

Example 3

A 300-ml four-necked flask equipped with a condenser, dropping funnel, thermometer, and magnetic stirrer was charged with 43.3 grams (0.208 mol) of 1,1,1-trifluoro-2-trifluoromethyl-4-penten-2-ol, 96.2 grams (1.04 mol) of epichlorohydrin, and 7.1 grams (0.021 mol) of tetrabutylammonium hydrogen sulfate. With stirring, the mixture was heated to 85° C. To the flask 55.5 grams (0.208 mol) of an aqueous solution of 15% weight sodium hydroxide was added dropwise over about 30 minutes and the mixture was stirred for a further 30 minutes at 85° C. The reaction mixture was allowed to separate into an organic layer and an aqueous layer. The organic layer (lower layer) was twice washed with water, dried over anhydrous sodium sulfate and collected by filtration. Vacuum distillation of this layer yielded 38.7 grams of the end product at a boiling point of 88°–90° C./47 mmHg. Based on the following analytical results, this product was found to be the fluorinated unsaturated glycidyl ether of formula (1b). The yield was 70%.

$$CH_2=CH-CH_2-\underset{\underset{CF_3}{F_3C}}{\overset{\phantom{x}}{C}}-O-CH_2-CH\overset{O}{\underset{\phantom{x}}{-}}CH_2 \qquad (1b)$$

Analytical results
$^{19}$F-NMR (CCl$_4$ solution, CF$_3$COOH standard): 4.3 ppm (s)

$^1$H-NMR (CCl$_4$ solution, TMS internal standard):

2.41–2.66 ppm (m, 2H, 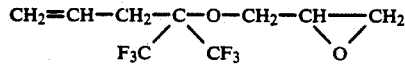)

2.71 ppm (d, 2H, $-CH_2-\underset{\underset{CF_3}{|}}{\overset{\overset{CF_3}{|}}{C}}-$)

2.89–3.11 ppm (m, 1H, 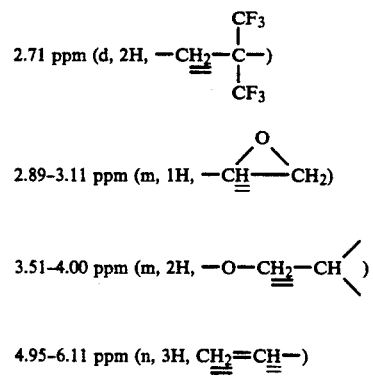)

3.51–4.00 ppm (m, 2H, $-O-CH_2-CH\diagdown$)

4.95–6.11 ppm (n, 3H, $CH_2=CH-$)

IR: FIG. 2

| | Elemental analysis: | | |
|---|---|---|---|
| | C | H | F |
| Calcd. (%) | 40.92 | 3.82 | 43.15 |
| Found (%) | 40.98 | 3.75 | 43.71 |

Example 4

A mixture of 1.0 grams (4.8 mmol) of 1,1,1,-trifluoro-2-trifluoromethyl-4-penten-2-ol, 2.2 grams (23.8 mmol) of chloromethyloxirane, 1.3 grams (4.9 mmol) of an aqueous solution of 15% by weight sodium hydroxide, and 0.5 mmol of the phase transfer catalyst shown in Table 2 was heated at 80° C. for 2 hours and then analyzed for composition by gas chromatography. The results are shown in Table 2.

TABLE 2

| Synthesis of $CH_2=CHCH_2\underset{\underset{CF_3}{F_3C}}{\overset{\phantom{x}}{C}}OCH_2CH\overset{O}{\underset{\phantom{x}}{-}}CH_2$ using phase transfer catalysts | | |
|---|---|---|
| Catalysts | Conversion of $CH_2=CH-\underset{\underset{CF_3}{F_3C}}{\overset{\phantom{x}}{C}}-OH$ (%) | Yield* of $CH_2-CH-\underset{\underset{CF_3}{F_3C}}{\overset{\phantom{x}}{C}}-O-CH_2CH\overset{O}{\underset{\phantom{x}}{-}}CH_2$ (%) |
| $(n-C_4H_9)_4NCl$ | 85 | 70 |
| $(n-C_4H_9)_4NBr$ | 80 | 75 |
| $C_6H_5CH_2(CH_3)_3NCl$ | 89 | 63 |
| $(n-C_4H_{25})N$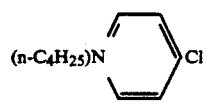Cl | 72 | 51 |

TABLE 2-continued

Synthesis of CH$_2$=CHCH$_2$COCH$_2$CH—CH$_2$ with F$_3$C, CF$_3$, O substituents using phase transfer catalysts

| Catalysts | Conversion of CH$_2$=CH—C(F$_3$C)(CF$_3$)—OH (%) | Yield* of CH$_2$—CH—C(F$_3$C)(CF$_3$)—O—CH$_2$CH—CH$_2$ (with O) (%) |
|---|---|---|
| (n-C$_4$H$_9$)$_4$PBr | 65 | 60 |

*calculated based on the consumed amount of CH$_2$=CH—C(F$_3$C)(CF$_3$)—OH

Example 5

A 100-ml stainless steel cylinder was charged with 25.0 grams (0.10 mol) of the compound of formula (1a), 14.7 grams (0.12 mol) of (CH$_3$O)$_3$SiH, and 0.024 grams (6.0×10$^{-5}$ mol) of Rh(CH$_2$COCHCOCH$_2$)$_3$ and heated at 135° C. for 10 hours. To the reaction mixture were additionally admitted 7.3 grams (0.06 mol) of (CH$_3$SiH and 0.024 grams (6.0×10$^{-5}$ mol) of Rh(CH$_2$COCH-COCH$_2$)$_3$. The mixture was heated at 135° C. for a further 10 hours. Distillation of the reaction mixture yielded 22.0 grams of the end product, which was found to be the compound of formula (2a) based on the following analytical results. The yield was 59%.

(CH$_3$O)$_3$SiCH$_2$CH$_2$COCH$_2$CH—CH$_2$ with CF$_3$, CF$_3$, O  (2a)

Analytical results
$^{19}$F-NMR (CF$_3$COOH standard): 4.9 ppm (s)

$^1$H-NMR (TMS internal standard):

0.64–0.93 ppm (m, 2H, ≡Si—C<u>H</u>$_2$—)

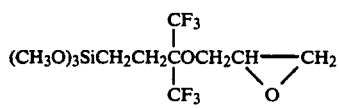

1.93–2.17 ppm (m, 2H, —C(CF$_3$)(CF$_3$)—C<u>H</u>$_2$—)

2.53–2.86 ppm (m, 2H, —C<u>H</u>—C<u>H</u>$_2$ with O)

3.06–3.17 ppm (m, 1H, —C<u>H</u>—CH$_2$ with O)

3.55 ppm (s, 9H, (C<u>H$_3$</u>O)$_3$Si—)

3.61–3.79 ppm (m, 2H, —O—C<u>H</u>$_2$—CH—)

IR (cm$^{-1}$): 3060 (w), 2955 (s), 2850 (s), 1458 (m), 1280 (s), 1210 (a), 1085 (s), 827 (s)

| | Elemental analysis: | | | |
|---|---|---|---|---|
| | C | H | F | Si |
| Calcd. (%) | 35.48 | 4.87 | 30.61 | 7.54 |
| Found (%) | 35.02 | 4.81 | 31.15 | 7.99 |

Example 6

A 25-ml stainless steel cylinder was charged with 1.0 gram (4.0 mmol) of the compound of formula (1a), 0.59 grams (4.8 mmol) of (CH$_3$O)$_3$SiH, and 4.8×10$^{-3}$ mmol of the catalyst shown in Table 3 and heated at 135° C. for 10 hours. The contents were analyzed for composition by gas chromatography. The results are shown in Table 3.

TABLE 3

Catalyzed Synthesis of (CH$_3$O)$_3$SiCH$_2$CH$_2$COCH$_2$CH—CH$_2$ with F$_3$C, CF$_3$, O

| Catalyst | Conversion of CH$_2$=CHCOCH$_2$CH—CH$_2$ (with F$_3$C, CF$_3$, O) (%) | Yield* of (CH$_3$O)$_3$SiCH$_2$CH$_2$COCH$_2$CH—CH$_2$ (with F$_3$C, CF$_3$, O) (%) |
|---|---|---|
| 2-ethylhexanol-modified H$_2$PtCl$_6$ | 100 | 0 |
| Rh(PPh$_3$)$_3$Cl | 75 | 22 |
| Rh(PPh$_3$)$_3$Br | 78 | 29 |
| Rh(OAc)$_4$ | 100 | 14 |
| Rh(PPh$_3$)$_2$(CO)Cl | 64 | 23 |
| Rh(PPh$_3$)$_3$(CO)H | 31 | 21 |

*calculated based on the consumed amount of CH$_2$=CHCOCH$_2$CH—CH$_2$ with F$_3$C, CF$_3$, O

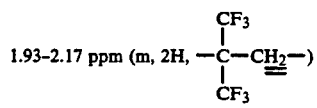
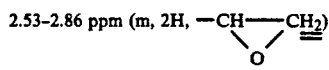

Example 7

A 200-ml three-necked flask equipped with a condenser, dropping funnel, thermometer, and magnetic stirrer was charged with 26.4 grams (0.10 mol) of the compound of formula (1b) and 0.011 grams (2.8×10$^{-5}$ mol) of Rh(CH$_2$COCHCOCH$_2$)$_3$ and heated to 85° C.

To the flask 17.1 grams (0.14 mol) of (CH$_3$O)$_3$SiH was added dropwise over 2 hours. The mixture was heated at 80° C. for a further 15 hours. Distillation of the reaction mixture yielded 25.5 grams of the end product, which was found to be the compound of formula (2b) based on the following analytical results. The yield was 66%.

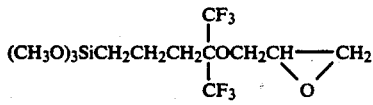
(2b)

Analytical results
$^{19}$F-NMR (CF$_3$COOH standard): 4.7 ppm (s)

$^1$H-NMR (TMS standard):

0.54–0.78 ppm (m, 2H ≡Si—C$\underline{H_2}$—)

1.47–2.11 ppm (m, 4H, —C$\underline{H_2}$—C$\underline{H_2}$—C—)
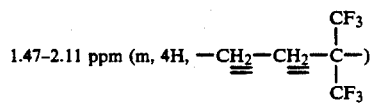

2.51–2.84 ppm (m, 2H, —CH——C$\underline{H_2}$)
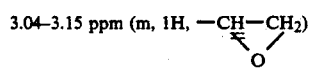

3.04–3.15 ppm (m, 1H, —C$\underline{H}$—CH$_2$)
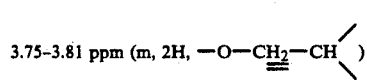

3.55 ppm (s, 9H, (C$\underline{H_3}$O)$_3$Si—)

3.75–3.81 ppm (m, 2H, —O—C$\underline{H_2}$—CH )

IR (cm$^{-1}$): 3060 (w), 2955 (s), 2850 (s), 1464 (m), 1274 (s), 1210 (a), 1090 (s), 818 (s)

| | Elemental analysis: | | | |
|---|---|---|---|---|
| | C | H | F | Si |
| Calcd. (%) | 37.30 | 5.22 | 29.50 | 7.27 |
| Found (%) | 36.98 | 5.10 | 28.85 | 7.51 |

Example 8

A 25-ml stainless steel cylinder was charged with 1.0 grams (3.8 mmol) of the compound of formula (1b), 0.59 grams (4.8 mmol) of (CH$_3$O)$_3$SiH, and 0.047 grams (4.8×10$^{-3}$ mmol) of 2-ethylhexanol-modified H$_2$PtCl$_6$ and heated at 100° C. for 15 hours. The contents were analyzed for composition by gas chromatography. The starting reactant, compound of formula (1b) had been completely consumed. There was obtained the compound of formula (2b) in a yield of 62%.

Example 9

By reacting 26.4 grams (0.10 mol) of the compound of formula (1b) with 14.6 grams (0.14 mol) of a compound of the following formula (4a) in accordance with the procedure of Example 7, 21.4 grams of a compound of the following formula (2c) was obtained in a yield of 58%.

(4a)

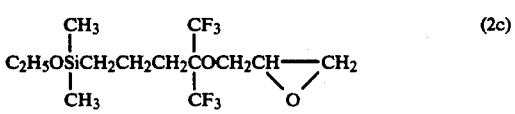
(2c)

Example 10

By reacting 26.4 grams (0.10 mol) of the compound of formula (1b) with 23.0 grams (0.14 mol) of (C$_2$H$_5$O)$_3$SiH in accordance with the procedure of Example 7, 29.1 grams of a compound of the following formula (2d) was obtained in a yield of 68%.

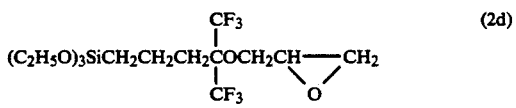
(2d)

Although some preferred embodiments have been described, many modifications and variation may be made thereto in the light of the above teachings. It is therefore to be understood that within the scope of the appended claims, the invention may be practiced otherwise than as specifically described.

We claim:
1. A fluorinated glycidyl ether of the following formula (1):

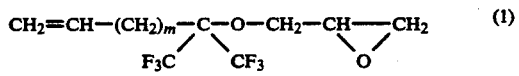
(1)

wherein m is equal to 0 or 1.

* * * * *